US006447659B1

(12) United States Patent
Peng

(10) Patent No.: US 6,447,659 B1
(45) Date of Patent: Sep. 10, 2002

(54) INTRINSIC SHORTING LINK FOR GAS SENSORS

(75) Inventor: Wenfeng Peng, Mississauga (CA)

(73) Assignee: Industrial Scientific Corporation, Oakdale, PA (US)

( * ) Notice: Subject to any disclaimer, the term of this patent is extended or adjusted under 35 U.S.C. 154(b) by 8 days.

(21) Appl. No.: 09/790,678

(22) Filed: Feb. 23, 2001

(51) Int. Cl.[7] .................... G01N 27/26

(52) U.S. Cl. .................... 204/424; 204/412; 204/418; 204/429; 204/431; 204/402

(58) Field of Search .................... 204/402, 412, 204/418, 429, 431, 424; 422/98, 83

(56) References Cited

U.S. PATENT DOCUMENTS 4,303,613 A * 12/1981 Yasuda et al. .......... 422/98
4,744,954 A * 5/1988 Campbell et al. .......... 422/98
5,000,180 A * 3/1991 Kuypers et al. .......... 204/412
6,055,840 A * 5/2000 Warburton .......... 73/1.06
6,370,940 B2 * 4/2002 Warburton .......... 204/424

* cited by examiner

*Primary Examiner*—Bruce F. Bell
(74) *Attorney, Agent, or Firm*—Dennison, Schultz & Dougherty

(57) ABSTRACT

An amperometric electrochemical gas sensor includes a permanent electrical resistance means disposed between two electrodes, one of which is the working electrode, the electrical resistance means having an electrical resistance of between about 10 Ω and 200 kΩ. This resistance means provides a permanent shorting link between the electrodes, and constantly maintains the sensor in a ready-to-work condition.

16 Claims, 5 Drawing Sheets

INTRINSIC SHORTING LINK FOR GAS SENSORS

BACKGROUND OF THE INVENTION

1. Field of the Invention

The present invention relates to electrochemical gas sensors operated in amperometric mode.

2. Description of Related Art

Electrochemical sensors for toxic gas detection operate in either amperometric or potentiometric mode, i.e. the output current or output voltage is measured as a function of gas concentration respectively. In order for an amperometric sensor to respond to the presence of a toxic gas, the working electrode of the sensor must be held at a potential where the gas can be effectively oxidized or reduced. The electrochemical reaction at the working electrode then generates a current dependent on and usually proportional to the gas concentration.

Amperometric gas sensors have at least a working electrode and a counter electrode. The working electrode provides a suitable catalyst for the electrochemical reaction (oxidation or reduction) of the target gas, while the counter electrode acts to balance out the reaction at the working electrode. If, for example, an oxidation reaction occurs at the working electrode, oxygen will be reduced to form water at the counter electrode. The current flowing through the counter and working electrodes is the same. The majority of amperometric sensors have a reference electrode in addition to a working electrode and a counter electrode. A reference electrode provides a stable, reference potential for the operation of the working electrode.

In order for the sensor to operate properly, the three electrodes are connected to a potentiostatic circuit in such a way that the working electrode potential is controlled vs. the reference electrode potential, and any current produced at the working electrode flows through the counter electrode so that the reference electrode remains un-polarized. Three electrode sensors are well known in the prior art, and are described, for example, in U.S. Pat. Nos. 3,776,832, 3,992,267, 3,824,167, and 3,909,386.

For sensors having only two electrodes, i.e. a working electrode and a counter electrode, the counter electrode also serves as a reference electrode. The catalyst material of this electrode is specially formulated so that polarization occurs to a lesser extent when current passes through the electrode.

The use of a platinum or other precious metal electrode as a reference electrode has greatly simplified gas sensor designs. The potential of a platinum reference electrode is believed to be controlled by the reduction of oxygen to water (1.23 V vs. standard hydrogen electrode under standard conditions, CRC Handbook of Chemistry and Physics, $68^{th}$ Edition, 1987–1988, CRC Press Inc, Boca Raton, Fla.) and the potential for this electrode is typically found to be about 1.0 V vs the standard hydrogen electrode. Quite a few toxic gases including carbon monoxide (CO), hydrogen sulfide ($H_2S$), sulfur dioxide ($SO_2$), hydrogen ($H_2$), hydrogen cyanide (HCN), phosphine ($PH_3$), silane ($SiH_4$) and ethylene oxide ($C_2H_4O$) can be readily oxidized at a potential significantly lower than this potential on an electrode with a suitably active catalytic surface. Some other gases such as nitrogen dioxide ($NO_2$), ozone ($O_3$), chlorine ($Cl_2$) and chlorine dioxide ($CO_2$) can be reduced at a potential significantly higher than this potential.

In order to detect these gases, the working electrode can be set at exactly the same potential as that of the reference electrode. Thus, a three-electrode cell can be operated with a bias of zero between the reference and working electrodes. The external electric circuitry eliminates the large potential difference between the working electrode and the reference electrode and ensures that the sensor is in working condition whether or not a target gas is present.

A two electrode cell can be operated with a zero bias voltage across the cell, either by means of a potentiostat, or more simply by adding a small load resistor (10–100_) between the two electrodes and measuring the voltage drop across the resistor.

Nevertheless, sensors are not always connected to external circuitry. New sensors often need to be stored for many weeks before being installed into an instrument. During the initial 4–12 weeks after manufacture, sensors undergo an important aging process through which their sensitivities drop by 10–30% to more stable values. Keeping electrodes shorted together accelerates this aging process. Gas sensors from instruments in the field are often returned for integrity tests, and some instruments are turned off when not in use.

When a sensor is disconnected from an instrument, its electrodes tend to polarize, i.e. develop a potential difference between them. The final potential difference between the working electrode and the reference or counter electrode depends on the catalytic materials and morphology of the electrodes, nature of the electrolyte, pH and surrounding atmosphere. The environment of the working electrode, which is exposed to the outside atmosphere is different from the reference electrode which is usually within the body of the sensor and thus separated from atmosphere by the electrolyte. Therefore, an open cell voltage between the working and reference electrodes gradually develops. For example, the open cell voltage of a carbon monoxide sensor may be as high as 0.3 volt in relatively clean air.

A large open cell voltage usually results in a high current spike when the sensor is connected to an instrument, and requires a long period of time for the sensor output current to stabilize before the instrument can be used. The time required for a cell to stabilize is referred to as the sensor "start-up", or "warm-up" time, and is usually somewhere between 15 minutes and more than 24 hours, depending on the type of cell.

In order to keep a sensor in a "ready to work" condition when the sensor is not connected to any powered circuitry, an electrical shorting link is usually added between working and reference electrodes to minimize polarization of the working electrode. The electrodes and electrolyte in the sensor cell and the external electric means constitute a complete, closed loop which allows current to flow from one electrode to the other. Preferably the electrical means has minimal resistance, so that the two electrode potentials are balanced within a short period of time. Existing shorting means include metal wires, metal springs, custom-made metal containing shorting links and conductive foams. The use of shorting clips is well known in the prior art, for example their use being discussed in U.S. Pat. Nos. 5,906,718, 6,001,240 and 6,074,539. A large current spike, typically at milliampere level, is usually observed upon connecting a shorting link to an open circuit sensor. The peak current is a function of the open cell voltage and the overall resistance in the closed circuitry. The current decays approximately exponentially to about zero when the sensor is surrounded by clean air. Internal and external shorting clips have also been described in U.S. Pat. No. 5,331,310 to combine the counter and reference electrodes in a three electrode electrochemical cell, for use in a two electrode cell circuit. However, in all the prior art examples of shorting clips, the intention was to reduce the resistance between the thus shorted electrodes to essentially zero.

While a shorting link is used in most amperometric gas sensors, manual connection and disconnection of this electric means has been very inconvenient, especially when hundreds or thousands of freshly produced sensors are to be stored and tested. Many gas detection instruments are used by personnel with only minimal training in the art of electrochemical gas sensors and sometimes the removal of the shorting pins is misunderstood or overlooked. Leaving the shorting pin in an instrument can cause a potentially dangerous situation. In addition to the costs associated with extra parts and labor, large current spikes may have a damaging effect on sensors themselves. In addition, most instruments must be designed with an electrical shorting means in place when they are un-powered, adding additional cost and complexity to the instruments. For example, U.S. Pat. No. 4,776,203 describes a potentiostat circuit including an electric connection between the sensing electrode and the working electrode. The connection is eliminated when the circuit is powered, with the making and breaking of the connection accomplished with a field effect transistor (FET) having a low resistance when turned off and a very high resistance when turned on. Similar electrode shorting devices associated with potentiostat circuits are disclosed in European Patent Application No. 220,896 and U.S. Pat. No. 4,776,203. Instead of using a FET, fixed resistors have also been incorporated into the potentiostat circuit. For example, U.S. Pat. No. 5,446,356 describes a potentiostat circuit for use in biasing a three-electrode electrochemical cell in which a direct electrical connection is made between the working electrode and the reference electrode during normal operation of the sensor. The use of an electrical connection in the potentiostat circuit reduces the zero gas current so that additional compensation circuitry is not required. These patents, however, do not offer any means of reducing start up times needed for a sensor not connected to any circuitry.

SUMMARY OF THE INVENTION

It is therefore an object of the invention to provide a shorting link for a gas sensor which is always in place, and which requires no adjustment or removal by personnel using the sensor.

It is a further object of the invention to provide a shorting link which reduces start-up time for new sensors.

To achieve these and other objects, the invention is directed to an amperometric electrochemical gas sensor comprising a permanent electrical resistance means disposed between the working electrode of the cell and an the reference electrode. In the case of a two electrode cell, the resistance means is disposed between the working electrode and the counter electrode, since the counter electrode also serves as a reference electrode. The electrical resistance of the permanent electrical resistance means is between about 10 Ω and 200 kΩ. This invention thus embodies incorporation of a permanent electrical pathway between the working electrode and at least one other electrode in the cell. The electrode shorting link is an electron-conductive medium, but has a finite resistance to current flow. Because the link is a permanent part of the sensor, it allows electrode potentials to be balanced within a relatively short period of time, but its resistance value is selected such that its presence does not affect the sensor response significantly.

DESCRIPTION OF THE PREFERRED EMBODIMENTS

Figure 1:
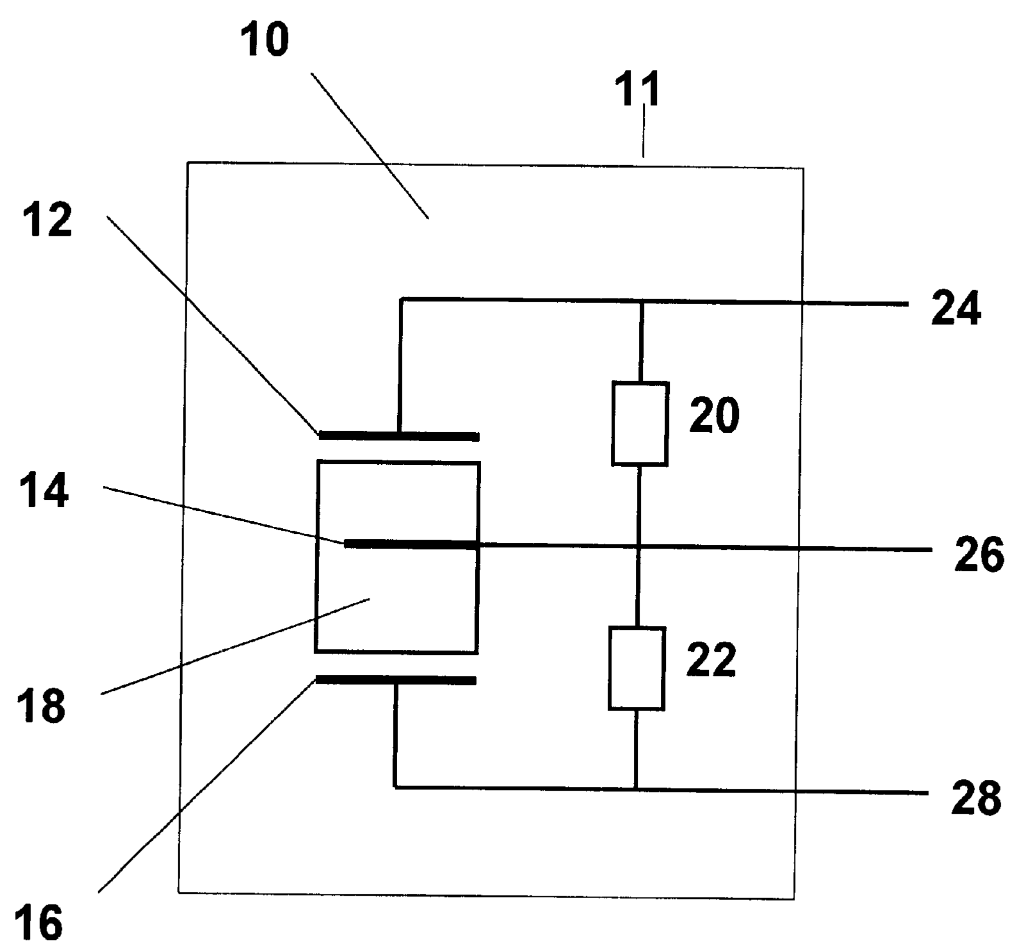
FIG. 1 is a schematic diagram of a three electrode electrochemical sensor incorporating fixed resistance elements between the working electrode and the reference electrode, and between the reference electrode and the counter electrode.

In a first embodiment shown in FIG. 1, a sensor 10 is disposed in a housing 11, and comprises a working electrode 12, a reference electrode 14, a counter electrode 16 and an ion-conductive electrolyte 18 which is in fluid contact with all electrodes. An electron conductive means 20 having a known resistance is connected between the working electrode 12 and the reference electrode 14. The resistance of the electronic conductive means is chosen between 10 Ω and 200 k Ωpreferably between 100 Ω and 10 kΩ. Another electron conductive means 22 of similar resistance is connected between the reference electrode 14 and the counter electrode 16. This second electron conductive means 22 is generally not necessary, but occurs inherently when the housing is formed of an electron conductive material, as discussed hereinbelow. The sensor 10 also includes a working electrode current collector 24, a reference electrode current collector 26 and a counter electrode current collector 28 to facilitate connections of the sensor to an electronic instrument.

Figure 2:
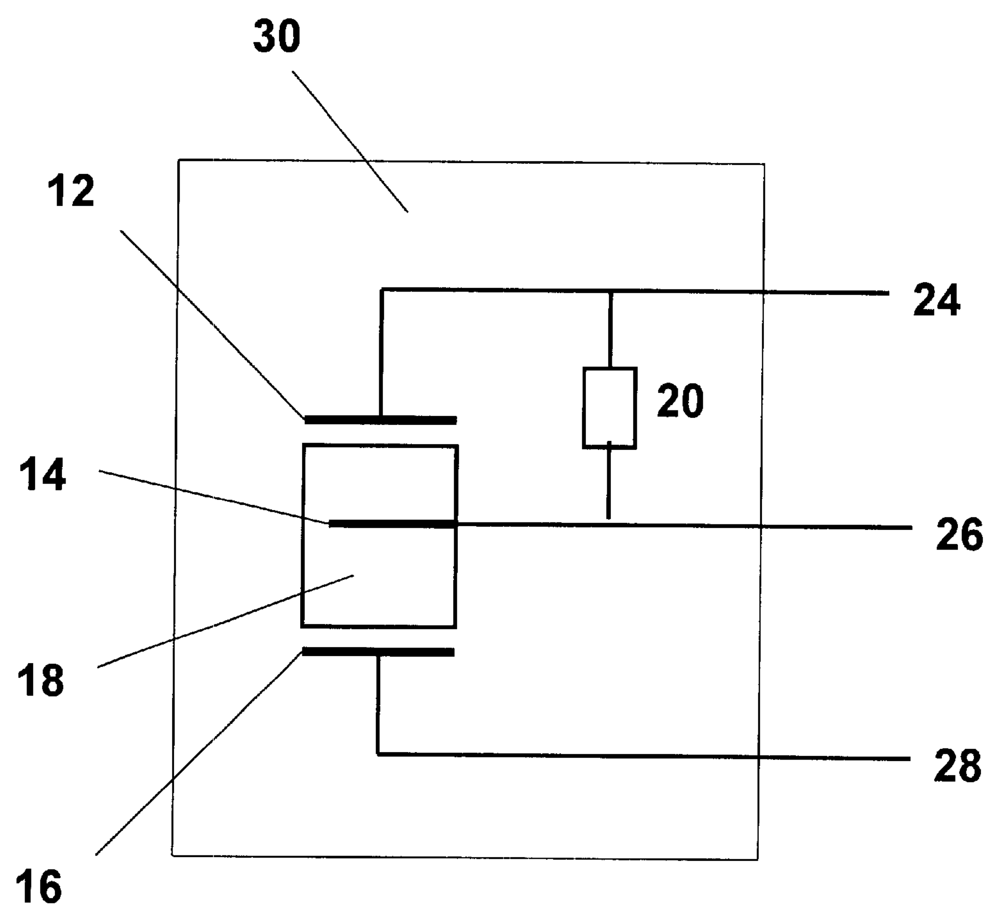
FIG. 2 is a schematic diagram of a three electrode sensor with a fixed resistance only between the working and reference electrodes.

The sensor 30 shown in FIG. 2 differs from sensor 10 shown in FIG. 1 in that no direct electrical connection, other than the electrolyte, exists between the reference electrode 14 and the counter electrode 16.

Figure 3:
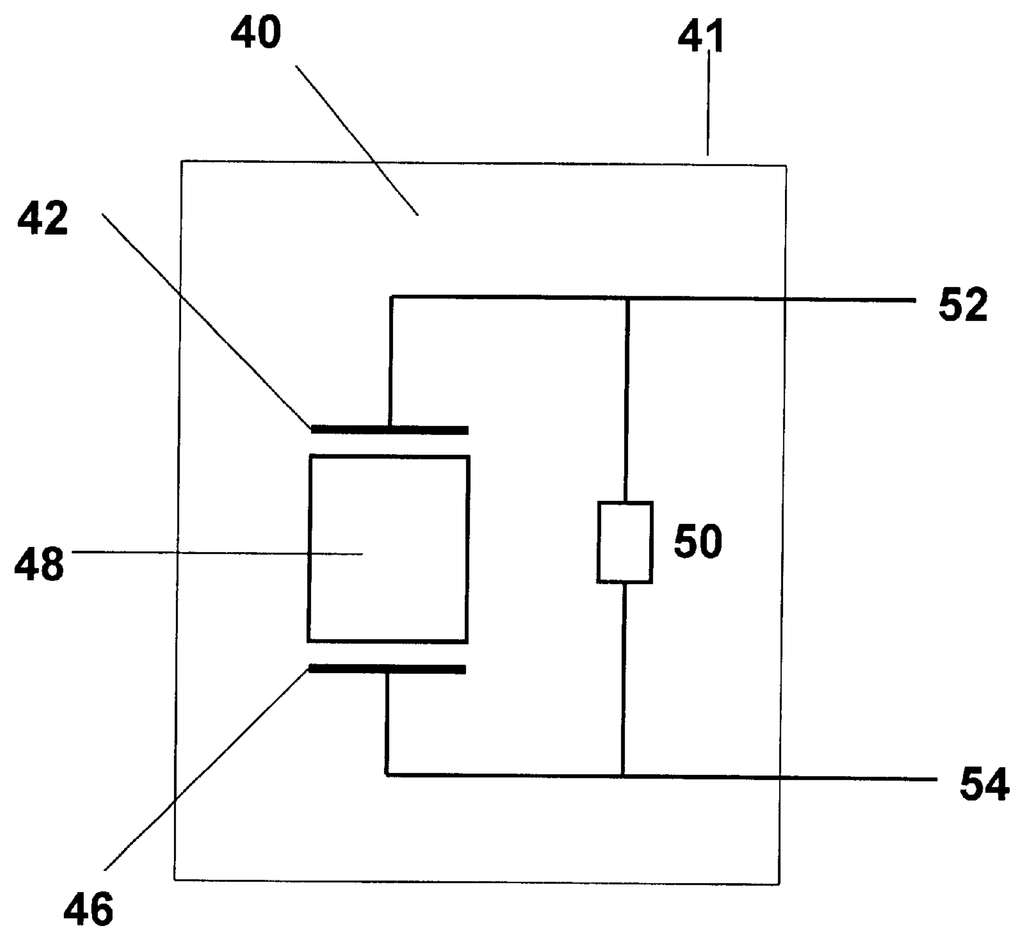
FIG. 3 is a schematic diagram of a two electrode sensor with a resistance between the working and counter electrodes.

Sensor 40 shown in FIG. 3 is a two electrode sensor including a working electrode 42, a counter electrode 46 and an ion-conductive electrolyte 48 which is in fluid contact with the working electrode 42 and the counter electrode 46. An electron conductive means 50 having appropriate electrical resistance is connected between the working electrode 42 and counter electrode 46. The sensor 40 has two current collectors 52 and 54 for connection of the working electrode 42 and the counter electrode 46, respectively, to any circuitry.

Sensors of the invention employ a built-in electrode shorting link, as illustrated in FIGS. 1, 2 and 3 as a permanent component in the sensor cell. The shorting means 20, 22 or 50 must meet two requirements:

1) it must be capable of bringing an open cell voltage to a few mV, and preferably below 1 mV within a reasonably short period of time, and
2) the use of the means must have no adverse effect on the sensor response, i.e. both sensor response time and amplitude of the output are about the same with or without the shorting means.

If the resistance is too small, then the sensor response is degraded and if the resistance is too large, then the time taken for the sensor to eliminate the large open cell voltage is too long. Experimentally, it has been found that the preferred value of the resistance of the shorting link is between 10 Ω and 200 kΩ, and most preferably between 100 Ω and 10 kΩ.

Amperometric sensors often employ a dilute acidic electrolyte, such as diluted sulfuric or phosphoric acid. Due to the corrosive nature of these electrolytes, the sensor housing is generally made of a plastic such as ABS, polyethylene, polycarbonate, Noryl® (a trademark of GE plastic), or other acid resistant plastic. Other components of the sensor are also designed to be acid resistant.

In one embodiment of the invention, in order to provide an electron conductive path between the electrodes, the plastic housing material is filled with a conductive component. For example, a polypropylene housing is filled with 10–30% (w/w) carbon fibers so that a specific resistance of 10 kΩ $cm^{-1}$ to 10 Ω $cm^{-1}$ is obtained. Such a filled resin material is available from RTP Company Winona, Minn.

As discussed above, the time required to reach equilibrium depends on the electrical resistance of the shorting means. The higher the resistance, the longer the time needed by the sensor to reach equilibrium. Preferably, the housing material is filled with 15% to 30% carbon fibers so that the material has a specific resistance greater than 10 Ω $cm^{-1}$ but not more than a few kΩ $cm^{-1}$. The use of a conductive plastic housing provides a direct shorting means between electrodes, in particular between the working and reference electrodes.

Alternatively, only a portion of the sensor housing is made conductive. Since most sensors have electrical contact pins molded in the sensor housing, the specific part of that housing can be made of conductive plastic while the rest of housing remains nonconductive. For example, some sensors have metal pins molded into the bottom of the sensor housing; a plastic plate made of a conductive plastic can be added underneath the bottom to provide a shorting link for the electrodes.

In another embodiment, a resistor can be added to a printed circuit board between the working and reference electrode pins to make a conductive link between the electrodes. The resistor can be added as an electric component, or simply screen-printed onto the circuit board. Because fine platinum wires are used inside most sensor cells, a circuit board having electrode contact pins is mounted to the bottom of the sensor to make an electrical connection to the platinum wires. The use of a circuit board allows a sensor to be used in instruments having different sensor configurations.

In a further embodiment, a conductive coating is applied externally onto a portion of housing where electrodes are disposed. The conductive paint may contain silver, copper, carbon, or any other electrically conductive material.

Figure 4:
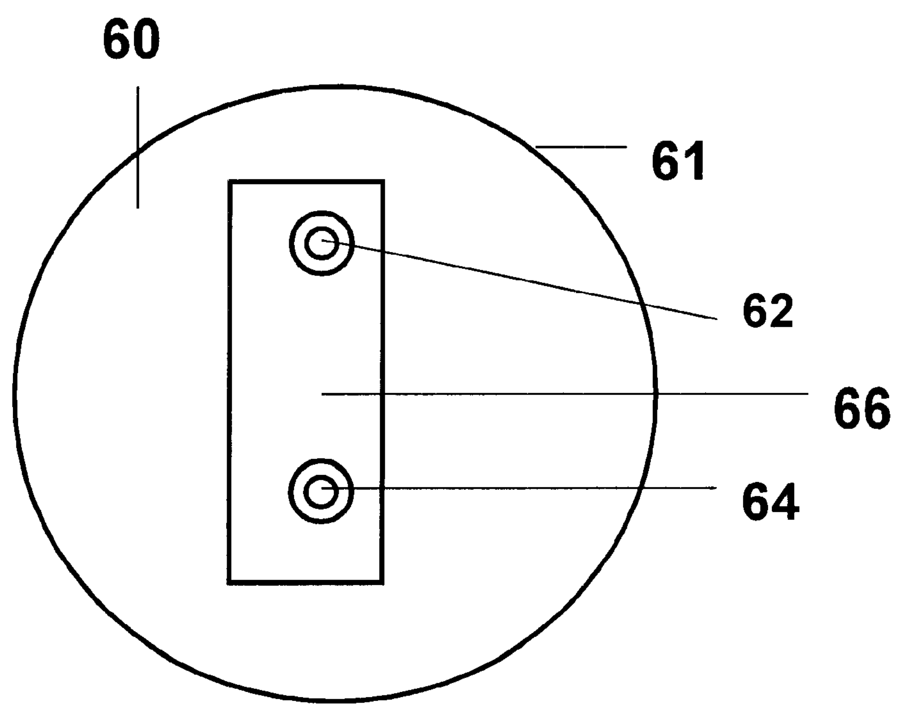
FIG. 4 is a bottom plan view of a two electrode gas sensor which is a variation of the embodiment shown in FIG. 3.

The above embodiments are shown generally in FIG. 4, a view of the bottom of a two electrode sensor unit 60. Current collector pins 62 and 64 protrude through the bottom of housing 61, in a resistive portion 66. This resistive portion 66 can be a coating on a plastic housing, a conductive plastic or a circuit board having a resistive portion between the current collectors.

Figure 5:
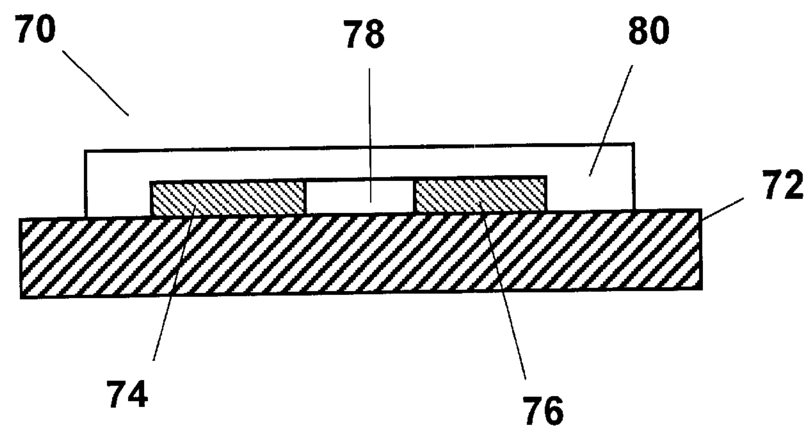
FIG. 5 is a side plan view with a portion in cross-section, of a two electrode gas sensor which is a variation of the embodiment shown in FIG. 3.

In a still further embodiment of the invention, an amperometric sensor comprising a solid electrolyte may be formed with a rigid support and may be formed directly on a circuit board, as disclosed, for example, in U.S. Pat. No. 5,437,999, on an electrical insulating substrate or on an electrically semiconductor substrate. Further, resistive electrical contacts may be formed between two or more of the electrodes by screen printing, electroless metallic deposition or vacuum deposition. This embodiment is shown in FIG. 5, in which a two electrode sensor 70 is formed directly on an insulating substrate 72 on which working electrode 74 and counter electrode 76 are formed. A screen printed resistive section 78 is formed between the electrodes on the substrate. The working electrode 74, the counter electrode 76 and the electrical resistance means 78 are coated by an ion-conductive electrolyte 80 such as Nafion® which is a proton-conductive perfluorinated polymer from Dupont.

Many other means for providing an electrical connection between two points are known to those skilled in the art of gas sensor construction and these and other means for providing resistive connections between electrodes may be used within the scope of this invention.

The use of conductive plastics is known in the art of gas sensor manufacture. As taught in U.S. Pat, Nos. 5,302,274, 5,744,697, 5,914,019, 6,099,708, and 6,129,825, some prior art sensors use a conductive plastic as current collectors in order to improve electrolyte leakage problems and simplify manufacturing. The conductive plastic that is in contact with an electrode typically has an electric resistance around 10–100 Ω $cm^{-1}$. In order to provide a direct shorting link between electrodes, the nonconductive plastic housing can be made of a plastic having a lower content of conductive agents such as 10%–25% carbon fiber that provide about 100 Ω to 100 kΩ resistance between electrodes, especially between the working and reference electrodes, or the working and counter/reference electrode for a two electrode sensor. The actual value of the resistance depends on the resistance of the conductive current collectors. For example, if the current collectors have a total resistance of 10 Ω, the resistance of the electrode shorting means is preferably between 200 Ω and 2 kΩ so that no more than 5% of current output is lost when detecting a target gas.

Sensors with two and three electrodes have been shown. Sensors with more than three electrodes are also known, particularly sensors with multiple working electrodes. For example, a four electrode sensor might have a first working electrode for carbon monoxide, a second working electrode for hydrogen sulfide, a reference electrode and a counter electrode. In this case, both working electrodes would advantageously be connected by resistance means to the reference electrode.

Most toxic gas detection instruments have an electric apparatus such as a J-FET or a ganged on/off stitch to short electrodes when the instruments are un-powered. A typical shorting J-FET has a resistance about a few hundred ohms. By using a shorting link of low resistance in the sensor, an electric shorting apparatus becomes unnecessary in the instrument as no voltage will be developed across the working and reference electrodes of the sensor. In addition to simpler circuit design and lower costs, the elimination of a shorting switch saves power, and reduces noise associated with un-smooth transitions between connections to the potentiostat and the shorting circuit which enable the instruments to give more accurate signals at low levels of gas concentration.

The electric link method, however, does not apply to sensors that require a bias voltage, and oxygen sensors which utilize a consumable reference electrode such as lead or zinc.

EXAMPLE 1

A variable resistor was connected in parallel with a two-electrode hydrogen sulfide sensor cell manufactured by Industrial Scientific Corporation, Oakdale, Pa. The sensor has an ABS housing and two metal pins molded in the bottom of the housing as current collectors. The two metal pins were shorted with the variable resistor and connected to a lab built potentiostat. A PC computer loaded with National Instruments LabVIEW™ software was used to record the output from the potentiostat as a function of time. The sensor was first exposed to clean air, then to 20 ppm $H_2S$ gas for 5 minutes. As shown in Table 1 below, the sensor sensitivity and response time in the presence of the 20 ppm $H_2S$ gas remained almost constant when the resistance was varied from infinite to 10 Ω. Meanwhile, no significant change was observed in the background current and the stability of the output current, indicating relative independence of the sensor response when resistance is greater than 10 Ω.

TABLE 1

| | Dependence of $H_2S$ sensor response on resistance of the electrode shorting means | | | | | | | | |
|---|---|---|---|---|---|---|---|---|---|
| Resistance, Ω | Open | 10K | 2K | 1K | 500 | 200 | 105 | 20 | 10 |
| Background μA | −0.309 | −0.153 | −0.139 | −0.164 | −0.202 | −0.239 | −0.236 | −0.255 | −0.257 |
| Sensitivity μA/ppm | 0.669 | 0.689 | 0.688 | 0.684 | 0.684 | 0.681 | 0.674 | 0.672 | 0.67 |
| T90, sec | 13 | 13 | 13 | 13 | 13 | 13 | 13 | 13 | 12 |
| Drift, % | −0.49 | 0.35 | 0.71 | 0.24 | 0.71 | 0.36 | 0.48 | −0.24 | −0.24 |

EXAMPLE 2

The open cell voltage for a three-electrode carbon monoxide sensor manufactured by City Technology Ltd, UK was found to be −245.5 mV (working electrode potential vs. reference electrode potential) in normal air measured with a Keithley Model 200 multimeter. When a 209 kΩ resistor was connected between the working and reference electrodes, the voltage started to increase at 0.005 mV/s. When using a 105 kΩ resistor, the starting rate of the voltage increase doubled. When using a 10.4 kΩ resistor, the starting rate of the voltage increase changed to 0.1 mV/s. The cell voltage continued to increase with time, and the rate of change decreased over time as it asymptoted to the steady state value of zero current.

With a 209 kΩ resistor, the cell voltage changed very slowly from −245.52 mV to −238.77 mV in 40 minutes. However, when the resistor was changed to 10 kΩ, the voltage changed from −238.77 mV to −123.67 mV after 1.5 hours, and after 12 more hours, the voltage increased to −21.93 mV. After 72 hours the voltage increased to and stabilized at −0.034 mV. However, when the resistor was removed, a larger cell voltage developed gradually across the cell.

This example shows that when the working and reference electrodes of a three electrode cell are shorted by an electron conductive means, the open cell voltage can be eliminated. The time necessary to eliminate the open cell voltage increases with increasing resistance of the electron conductive means.

What is claimed is:

1. An amperometric electrochemical gas sensor comprising at least a working electrode, a reference electrode, and an electrolyte disposed within a sensor housing, said sensor further comprising a permanent electrical resistance means disposed between the working electrode and the reference electrode, the electrical resistance means having an electrical resistance of between about 10 Ω and 200 kΩ.

2. The sensor of claim 1, wherein the electrical resistance means has an electrical resistance between about 100 Ω and 10 kΩ.

3. The sensor of claim 1, which is a two electrode sensor, wherein the permanent electrical resistance means is disposed between the working electrode and a counter electrode which serves as a reference electrode.

4. The sensor of claim 1, which comprises at least three electrodes, including a working electrode, a counter electrode and a reference electrode.

5. The sensor of claim 4, additionally comprising at least one further permanent electrical resistance means disposed between two said electrodes of the sensor.

6. The sensor of claim 5, wherein the at least one further permanent electrical resistance means has an electrical resistance of between about 10 Ω and 200 kΩ.

7. The sensor of claim 5, wherein the further electrical resistance means is disposed between the counter electrode and the reference electrode.

8. The sensor of claim 5, wherein the further electrical resistance means is disposed between the working electrode and the counter electrode.

9. The sensor of claim 1, wherein the electrical resistance means is made of a conductive plastic.

10. The sensor of claim 9, wherein the conductive plastic contains 10 to 30% by weight carbon.

11. The sensor of claim 9, wherein the conductive plastic forms at least a portion of the sensor housing, and has a specific resistance of 10 Ω $cm^{-1}$ to 200 kΩ $cm^{-1}$.

12. The sensor of claim 9, wherein the conductive plastic is permanently mounted on the sensor housing in the vicinity of electrode contact pins.

13. The sensor of claim 1, additionally comprising a current collector in electrical connection with each said electrode, wherein the electrical resistance means is disposed between the working electrode current collector and the reference electrode current collector.

14. The sensor of claim 13, wherein the current collectors comprise contact pins protruding from a circuit board mounted on a portion of the sensor housing, and the electrical resistance means is disposed between the contact pins.

15. The sensor of claim 13, wherein the electrical resistance means comprises an electrically conductive coating applied to the potion of a sensor housing in the vicinity of said current collectors.

16. The sensor of claim 1, wherein the electrical resistance means comprises a screen printed electrically conductive material disposed on an insulating substrate which forms part of the sensor housing.

* * * * *